US00PP14194P39

(12) United States Plant Patent
Meilland

(10) Patent No.: US PP14,194 P3
(45) Date of Patent: Sep. 30, 2003

(54) MINI-FLORA ROSE PLANT NAMED 'MEIPTIPIER'

(50) Latin Name: *Rosa hybrida*
Varietal Denomination: 'Meiptipier'

(75) Inventor: Alain A. Meilland, Antibes (FR)

(73) Assignee: CP (Delaware), Inc., Wilmington, DE (US)

( * ) Notice: Subject to any disclaimer, the term of this patent is extended or adjusted under 35 U.S.C. 154(b) by 0 days.

(21) Appl. No.: 09/984,848

(22) Filed: Oct. 31, 2001

(65) Prior Publication Data

US 2003/0084491 P1 May 1, 2003

(51) Int. Cl.[7] ..... A01H 5/00
(52) U.S. Cl. ..... Plt./141
(58) Field of Search ..... Plt./141, 142, 102, Plt./107, 123

(56) References Cited

PUBLICATIONS

UPOV–RoM, 2002/02, Plant Variety Database GTI Jouve Retrieval Software, citation for 'Meiptipier'.*

Protection des Obtentions Vegetales, Bulletin Officiel du Comité de la Protection des Obtentions Végétales, Cover Pages and pp. 47, 49, and 55 (Feb. 2000).

Protection des Obtentions Vegetales, Bulletin Officiel du Comité de la Protection des Obtentions Végétales, Cover Page and pp. 217 and 222 (May 2000).

* cited by examiner

*Primary Examiner*—Howard J. Locker
(74) *Attorney, Agent, or Firm*—Burns, Doane, Swecker & Mathis, L.L.P.

(57) ABSTRACT

A new and distinct variety of rose plant of the Mini-Flora Class is provided which abundantly forms attractive double bicolored blossoms that are deep rosy pink on the inner petals and pale ivory pink on the outer petals. The buds are globose in configuration and are borne on stems having relatively few thorns. An open vase-shaped growth habit is exhibited. The foliage is matte medium to dark green and contrasts nicely with the bicolored pink blossoms. The new variety is well suited for the production of cut flowers under greenhouse growing conditions.

2 Drawing Sheets

Figure 1:
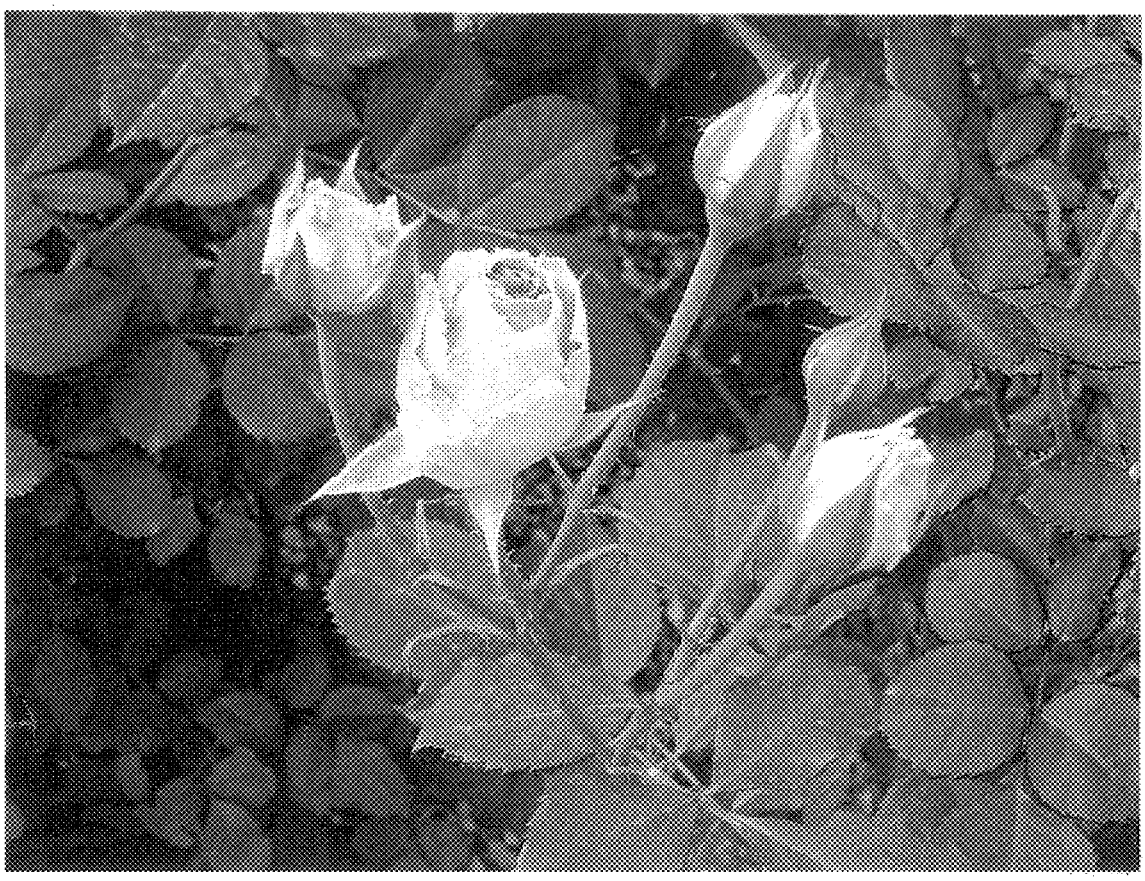

Botanical/Commercial Classification: Rosa hybrida/Mini-Flora Rose Plant.
Varietal Denomination: 'Meiptipier'.

SUMMARY OF THE INVENTION

The new variety of Rosa hybrida Mini-Flora rose plant was created by artificial pollination wherein two parents were crossed which previously had been studied in the hope that they would contribute the desired characteristics. Alternatively, the new variety could be termed a Miniature Floribunda. The female parent (i.e., the seed parent) of the new variety was the product of the cross of the 'Interniki' variety (U.S. Plant Pat. No. 8,114) and 'Olijdum' variety (U.S. Plant patent application Ser. No. 09/293,176, filed Apr. 16, 1999). The male parent (i.e., the pollen parent) of the new variety was the product of the cross of the 'Meichevil' variety (U.S. Plant Pat. No. 7,334) and the 'Keinoumi' variety (U.S. Plant Pat. No. 8,484). The parentage of the new variety can be summarized as follows:

('Interniki'×'Olijdum')×('Meichevil'×'Keinoumi').

The seeds resulting from the above pollination were sown and small plants were obtained which were physically and biologically different from each other. Selective study resulted in the identification of a single plant of the new variety.

It was found that the new variety of Mini-Flora rose plant of the present invention possesses the following combination of characteristics:

(a) forms generally globose buds in the form of a spray on stems having relatively few thorns, (b) forms in abundance attractive double bicolored blossoms that are deep rosy pink on the central petals and pale ivory pink on the outer petals, (c) is a vigorous grower and exhibits an open vase-shaped growth habit, and (d) forms attractive matte medium to dark green foliage upon maturity.

The bicolored spray inflorescence coloration contrasts nicely with the dense medium to dark green foliage.

The new variety of the present invention can be readily distinguished from its ancestors. More specifically, the 'Interniki' variety displays medium red flowers and glossy foliage, the 'Olijdum' variety displays dark red flowers, the 'Meichevil' variety displays dark pink flowers, and the 'Keinoumi' variety displays dark red flowers that are borne on long stems.

The new variety well meets the needs of the horticultural industry. It is well suited for use in the production of cut floral sprays under greenhouse growing conditions.

The new variety has been found to undergo asexual propagation in France and at West Grove, Pa. by the rooting of cuttings. Asexual propagation by the use of cuttings as performed in France and at West Grove, Pa. has shown that the characteristics of the new variety are strictly transmissible from one generation to another.

The new variety has been named the 'Meiptipier' variety.

BRIEF DESCRIPTION OF THE PHOTOGRAPHS

The accompanying photographs show as nearly true as it is reasonably possible to make the same, in color illustrations of this character, typical specimens of the new variety. The rose plants of the new variety were approximately eighteen months of age and were observed during October while growing in containers on their own roots in greenhouses at West Grove, Pa.

FIG. 1—illustrates a spray of buds in various stages of opening as well as the mature foliage that displays a matte finish. Anthocyanin coloration is apparent on some of the younger leaflets that are included in the photograph as well as on the margins of maturing leaflets.

Figure 2:
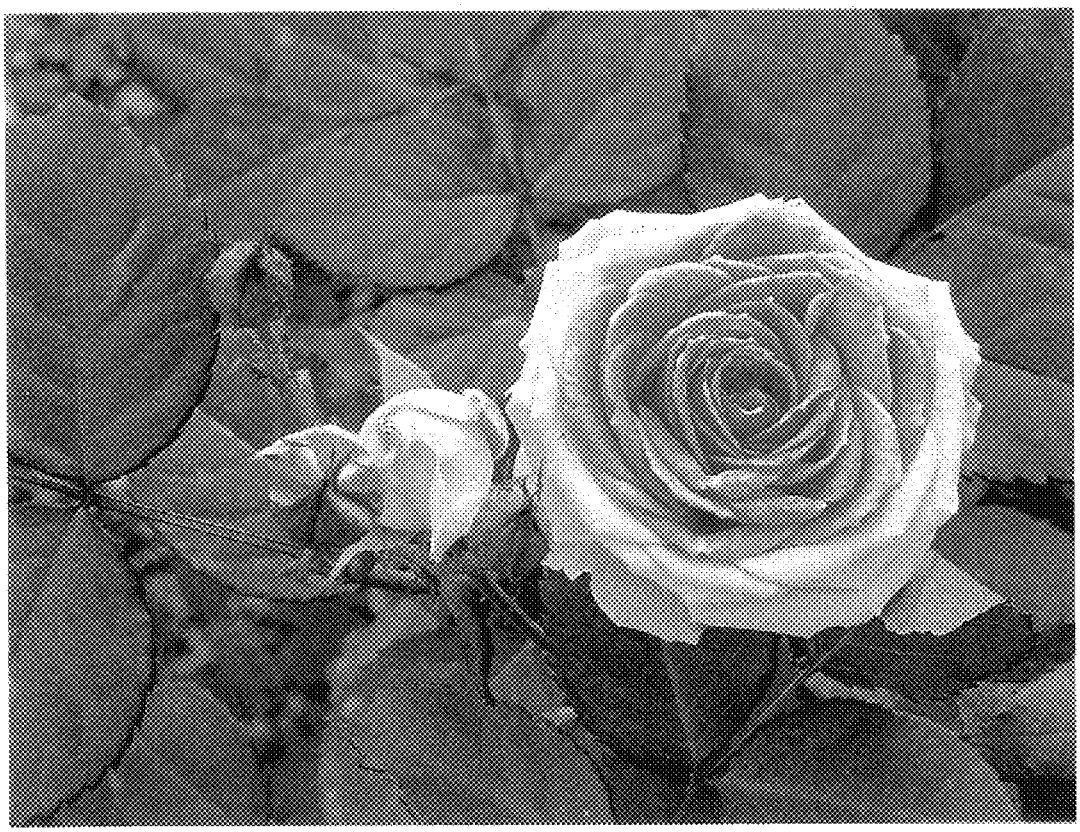

FIG. 2—illustrates at the right a close view of an open flower. The bicoloration of the petals is shown wherein the central petals are a deep rosy pink and the outer petals are a pale ivory pink. Typical buds and foliage are included in the photograph.

DETAILED DESCRIPTION

The chart used in the identification of the colors is that of The Royal Horticultural Society (R.H.S. Colour Chart). When more common color terms are utilized they are to be accorded customary dictionary significance. The description is based on eighteen month-old specimens of the new variety which were observed during October while growing in containers on their own roots in greenhouses at West Grove, Pa.

Class: Mini-Flora.

Plant:

*Height.*—Commonly assumes a height of approximately 57 to 83 cm at the end of the growing season.

*Width.*—Commonly approximately 90 to 110 cm at the end of the growing season. However, such width commonly is not achieved as flowers are produced and harvested during the growing season.

*Habit.*—Open and vase-shaped.

Branches:

*Thorns.*—Size: average approximately 0.7 cm in length. Quantity: few (approximately 1.6 prickles per linear inch from the base of current growth to the first flowering bud) on flowering stems and frequently present on the ventral side of the rachis. Configuration: somewhat straight upper surface and slightly concave under surface. Color: prickles on the terminal three inches of a young shoot bear a noticeable reddish-pink coloration of Red-Purple Group 63A to 63B. On mature shoots the prickles are near Grey-Brown Group 199A in coloration and average approximately 10.8 mm in length.

*Young stems.*—Flowering stems commonly are approximately 60 to 75 cm in length, and near Green Group 137B and 137C in coloration.

*Adult wood.*—Initially near Green Group 137C to Yellow-Green Group 143A, and with greater maturity changing to near and through Greyed-Orange Group 177A, Grey-Brown Group 199A and 199B, and Brown Group 200D. The fully mature bark commonly assumes a corky appearance.

Leaves:

*Leaflets.*—Number: 3, 5, and 7 (most often) in a ratio of approximately 1:2:3. Shape: generally elliptic with a generally symmetrical acute tip and an obtuse base. Texture: glabrous. Serration: simple and regular (as illustrated). General appearance: medium to dark green with a matte finish when fully mature. The newest immature leaflets display a glossy surface that later becomes semi-glossy with some maturity. Color (young foliage): Upper surface: Green Group 138A and 138B with an overlay of near Greyed-Purple Group 187A which tends to be more strongly visible towards the margins. Under surface: near Greyed-Green Group 191A with an overlay of near Greyed-Purple Group 183A and 183B. Color (adult foliage): Upper surface: near Green Group 139A. During maturation there commonly is some Greyed-Purple coloration. The fully mature foliage commonly shows no discernable Greyed-Purple pigmentation. Under surface: near Greyed-Green Group 191B to 191C with margins commonly approaching Greyed-Green Group 191A. During maturaton there may be a slight amount of Greyed-Purple Group187C that overlays the green mostly at the edge of the margins. The fully mature foliage commonly shows no discernable red pigmentation.

Inflorescence:

*Number of flowers.*—Range from rarely solitary (one bloom per inflorescence) to as many as 40 blooms in a compound cyme. The number of blossoms varies with the season and plant vigor.

*Peduncle.*—Near Green Group 137B and 137C in coloration.

*Sepals.*—Number: five. Size: commonly average approximately 22 mm in length and approximately 5.3 mm in width at the base. Extensions: from 0 to 2 and rarely 3 foliaceous extensions commonly on present on each sepal which commonly range from approximately 2 to 5.5 mm in length. Color: on the inside surface near Greyed-Green Group 192C and densely pubescent, and on the outside surface primarily Green Group 137C along the midvein and shading to Green Group 137B towards the edges. A small amount of Greyed-Purple Group 187B sometimes is displayed at the margin and tip.

*Buds.*—Shape: globose.

*Flower.*—Form: cup-shaped when fully open. Diameter: approximately 4.5 to 6 cm and approximately 5 cm on average. Color: on the upper surface the central petals are primarily Red-Purple Group 66C with tones of Red-Purple Group 67C and 68A. The most distal portion of the petal and margin commonly shades to Red-Purple Group 66B. As the blossoms reach full maturity, the central petal coloration lightens somewhat to near Red-Purple Group 62A towards the margins and shades near and through Red-Purple Group 62A, 62C, 65A, 65D, 68B, and 68C, and to near White Group 155A and 155B with some light pink tones near the base. The outer petals are pale ivory pink, White Group 155A and 155B with shades of light pink. The lightest colored petals are present towards the outside of the blooms causing the fully open blooms to display a bicolored appearance when viewed from above. On the under surface the most distal portion of the petal and margin commonly is near Red-Purple Group 67B and shades to near and through Red-Purple Group 62A, 62C, 65A, 65D, and 68B to near White Group 155C at the petal base. Fragrance: slight. Petal number: approximately 27 to 40 with an average of approximately 32. Petal configuration: broadly obovate with a broadly cuneate base and a broadly obtuse to mucronate apex. As the petals mature they tend to become revolute, particularly at distal one-half. Petaloids: approximately 5 to 11 small petaloids with an average of approximately 7 are typically present per bloom. Such petaloids sometimes appear to be fused to the anthers. Pistil number: commonly approximately 25 to 50 on average. Pistil length: approximately 10 mm. Pistil color: Orange-White Group 159A and 159B. Stamen number: commonly approximately 50 to 75. Anther length: approximately 1.2 to 1.5 mm. Anther color: near Brown Group 200A. Pollen: none observed to date. Petal drop: good, the petals commonly detach cleanly. Lasting quality: long, with blossoms commonly lasting up to approximately 24 days on the plant under greenhouse growing conditions. When cut and placed in a vase the blossoms commonly last approximately 10 to 14 days.

Development:

*Vegetation.*—Strong.

*Blooming.*—Abundant.

*Resistance to diseases.*—Good with respect to Powdery Mildew and Rose Rust under standard greenhouse growing conditions.

*Aptitude to bear fruit.*—None observed with plants having been closely pruned to date.

I claim:

1. A new and distinct variety of Mini-Flora rose plant characterized by the following combination of characteristics:

(a) forms generally globose buds in the form of a spray on stems having relative few thorns, (b) forms in abundance attractive double bicolored blossoms that are deep rosy pink on the central petals and pale ivory pink on the outer petals, (c) exhibits an open vase-shaped growth habit, and (d) forms attractive matte medium to dark green foliage upon maturity;

substantially as herein shown and described.

* * * * *